US011932209B2

(12) United States Patent
Liu et al.

(10) Patent No.: US 11,932,209 B2
(45) Date of Patent: Mar. 19, 2024

(54) METHOD AND SYSTEM FOR PROTECTING OPERATION OF TRAIN UNDER AIR POLLUTION ENVIRONMENT

(71) Applicant: CENTRAL SOUTH UNIVERSITY, Hunan (CN)

(72) Inventors: Hui Liu, Hunan (CN); Chao Chen, Hunan (CN); Guangxi Yan, Hunan (CN); Zhihao Long, Hunan (CN)

(73) Assignee: Central South University, Hunan (CN)

( * ) Notice: Subject to any disclaimer, the term of this patent is extended or adjusted under 35 U.S.C. 154(b) by 179 days.

(21) Appl. No.: 17/311,992

(22) PCT Filed: Jul. 29, 2020

(86) PCT No.: PCT/CN2020/105470
§ 371 (c)(1),
(2) Date: Jun. 8, 2021

(87) PCT Pub. No.: WO2021/023074
PCT Pub. Date: Feb. 11, 2021

(65) Prior Publication Data
US 2022/0153236 A1 May 19, 2022

(30) Foreign Application Priority Data
Aug. 2, 2019 (CN) .......................... 201910709594.6

(51) Int. Cl.
*B60S 3/00* (2006.01)
*G01N 17/00* (2006.01)
(Continued)

(52) U.S. Cl.
CPC ............ *B60S 3/006* (2013.01); *G01N 17/006* (2013.01); *G01N 17/008* (2013.01);
(Continued)

(58) Field of Classification Search
None
See application file for complete search history.

(56) References Cited

U.S. PATENT DOCUMENTS

2016/0091474 A1\* 3/2016 Griffon ............. G01N 33/0036
702/24
2016/0290979 A1\* 10/2016 Cogill .................. G01N 33/004
(Continued)

FOREIGN PATENT DOCUMENTS

CN  105655067 A  \*  6/2016
CN  105655067 A     6/2016
(Continued)

OTHER PUBLICATIONS

English abstract of CN105655067A.
(Continued)

*Primary Examiner* — Spencer E. Bell
*Assistant Examiner* — Omair Chaudhri
(74) *Attorney, Agent, or Firm* — Caesar Rivise, PC

(57) ABSTRACT

The present invention discloses a method and system for protecting the operation of a train under an air pollution environment. The method for protecting the operation of the train under the air pollution environment comprises: acquiring multiple groups of roof and underbody air quality detection data; solving comprehensive roof and underbody air evaluation indicator $Q_0$ and $Q_1$ by using the experimental data; calculating an exposure time $T_0$ of roof components and an exposure time $T_1$ of underbody components; training a calculation model of pollutant condition about roof component and a calculation model of pollutant condition about underbody component; detecting roof and underbody air quality detection data after the train stops; calling the trained roof and calculation model of pollutant condition about underbody components, and solving roof and underbody component pollution levels, and performing corresponding
(Continued)

cleaning on the roof and underbody components according to the solved roof and underbody component pollution levels. The present invention evaluates the exposed status of key components of the train under the air pollution environment, and takes relevant protective measures to ensure normal service lives of the key components of the train.

10 Claims, 2 Drawing Sheets

(51) Int. Cl.
    *G01N 33/00* (2006.01)
    *G06F 18/214* (2023.01)
(52) U.S. Cl.
    CPC ..... *G01N 33/0034* (2013.01); *G01N 33/0062* (2013.01); *G06F 18/214* (2023.01)

(56) References Cited

U.S. PATENT DOCUMENTS

| | | | |
|---|---|---|---|
| 2019/0118140 A1* | 4/2019 | Fingland | F01P 7/12 |
| 2019/0291699 A1* | 9/2019 | Nakatsuka | B08B 3/02 |
| 2020/0003437 A1* | 1/2020 | Breen | A61B 5/7275 |
| 2021/0140930 A1* | 5/2021 | Si | G08G 1/20 |
| 2021/0291614 A1* | 9/2021 | Liu | B60H 1/00849 |
| 2022/0153320 A1* | 5/2022 | Liu | B61D 27/00 |
| 2022/0234549 A1* | 7/2022 | Schütz | B60S 3/008 |

FOREIGN PATENT DOCUMENTS

| | | | | |
|---|---|---|---|---|
| CN | 106129889 A | | 11/2016 | |
| CN | 106960285 A | | 7/2017 | |
| CN | 107167178 A | | 9/2017 | |
| CN | 107167178 B | * | 7/2019 | ............ G01D 21/02 |
| CN | 110333325 A | | 10/2019 | |
| JP | 2000193651 A | * | 7/2000 | |
| JP | 2000193651 A | | 7/2000 | |
| JP | 2006127100 A | * | 5/2006 | |
| JP | 2006127100 A | | 5/2006 | |
| KR | 100797057 B1 | * | 1/2008 | |
| KR | 20090053028 A | * | 5/2009 | |
| KR | 20120108671 A | * | 10/2012 | |

OTHER PUBLICATIONS

English abstract of CN106129889A.
English abstract of CN106960285A.
English abstract of CN107167178A.
English abstract of CN110333325A.
English abstract of JP2000193651A.
English abstract of JP2006127100A.
International Search Report for corresponding PCT Application No. PCT/CN2020/105470 dated Nov. 4, 2020.

* cited by examiner

METHOD AND SYSTEM FOR PROTECTING OPERATION OF TRAIN UNDER AIR POLLUTION ENVIRONMENT

CROSS-REFERENCE TO RELATED APPLICATIONS

This application is a U.S. National Phase Application under 35 U.S.C. § 371 of PCT/CN2020/105470, filed Jul. 29, 2020, which claims priority from Chinese Patent Application No. CN201910709594.6, filed Aug. 2, 2019, the contents of which applications are incorporated herein by reference in their entireties.

FIELD OF THE INVENTION

The present invention particularly relates to a method and system for protecting the operation of a train under an air pollution environment.

BACKGROUND OF THE INVENTION

High-speed trains have developed rapidly in China in recent years. High-speed train transportation is one of the resource-based and environment-friendly transportation modes. Speeding up the development of high-speed trains has now become a consensus in all aspects of society. High-speed trains have become the artery of China's national economic development, with the characteristics of safety, economy, convenience and the like. These characteristics determine their transformation to mass transportation, and enable them to be the backbone of China's comprehensive transportation system.

However, with the expansion of high-speed train operating networks and the increase in operating mileage year by year, some problems have also been exposed. Among them, the air pollution environment is particularly harmful to exposed key components of high-speed trains. When the content of $SO_2$, $NO_2$, or the like in the train operating environment is too high, the problems of pitting and corrosion of exposed key components such as pantograph components, contact networks, and bogies may be aggravated, thereby shortening the service lives of the exposed key components and causing economic losses.

SUMMARY OF THE INVENTION

The purpose of the present invention is to provide a method and system for protecting the operation of a train under an air pollution environment, which evaluate the exposure situation of key components of the train under the air pollution environment, and take relevant protective measures to ensure normal service lives of the key components of the train.

In order to solve the above technical problems, the technical solution adopted by the present invention is:

A method for protecting the operation of a train under an air pollution environment, characterized by including the following steps:

step 1, acquiring multiple groups of roof air quality detection data and underbody air quality detection data, and calculating an average concentration of each pollutant on the roof and underbody of the train during an operating time from the time leaving a departure station to a current time;

step 2, solving a comprehensive roof air evaluation indicator $Q_0$ by using the roof air quality detection data in step 1, and solving a comprehensive underbody air evaluation indicator $Q_1$ by using the underbody air quality detection data in step 1;

step 3, calculating an exposure time $T_0$ of roof components under the condition of $Q_0 \geq Q$, and calculating an exposure time $T_1$ of underbody components under the condition of $Q_1 \geq Q$; wherein Q is a set health value of comprehensive air quality evaluation indicator;

step 4, training a calculation model of pollutant condition about roof component according to the following method:

simulating the operation of the train by using the average concentration, calculated in step 1, of each pollutant on the roof of the train during the operating time from the time leaving the departure station to the current time and the $T_0$ correspondingly solved in step 3 as experimental simulation conditions to obtain a pollution level $G_0$ of the roof components under different experimental simulation conditions, wherein the pollution grade of the roof components is classified as G levels; and training the calculation model of pollutant condition about roof component by using the average concentration, calculated in step 1, of each pollutant on the roof of the train during the operating time from the time leaving the departure station to the current time and the $T_0$ correspondingly solved in step 3 as an input and using $G_0$ as an output to obtain a trained calculation model of pollutant condition about roof component;

training a calculation model of pollutant condition about underbody component according to the following method:

simulating the operation of the train by using the average concentration, calculated in step 1, of each pollutant on the underbody of the train during the operating time from the time leaving the departure station to the current time and the $T_1$ correspondingly solved in step 3 as experimental simulation conditions to obtain a pollution level $G_1$ of the underbody components under different experimental simulation conditions, wherein the pollution grade of the underbody components is classified as G levels; and training the calculation model of pollutant condition about underbody component by using the average concentration, calculated in step 1, of each pollutant on the underbody of the train during the operating time from the time leaving the departure station to the current time and the $T_1$ correspondingly solved in step 3 as an input and using $G_1$ as an output to obtain a trained calculation model of pollutant condition about underbody component;

step 5, acquiring, after the train stops, roof air quality detection data and underbody air quality detection data;

step 6, by using the roof air quality detection data in step 5, solving an average concentration of each pollutant on the roof of the train during the operating time from the time leaving the departure station to the current time, a comprehensive roof air evaluation indicator $Q_0$, and an exposure time $T_0$ of the roof components under the condition of $Q_0 \geq Q$; and calling the trained calculation model of pollutant condition about roof component under the condition of $Q_0 \geq Q$ to solve a roof component pollution level; and by using the underbody air quality detection data in step 5, solving an average concentration of each pollutant on the underbody of the train during the operating time from the time leaving the departure station to the current time, a comprehensive underbody air evaluation indicator $Q_1$, and an exposure time $T_1$ of the underbody components under the condition of $Q_1 \geq Q$; and calling the trained calculation model of pollutant condition about underbody component under the condition of $Q_1 \geq Q$ to solve an underbody component pollution level; and step 7, performing corresponding cleaning on the roof components according to the pollution level, solved in step 6, of the roof components; and performing corresponding cleaning on the underbody components according to the pollution level, solved in step 6, of the underbody components.

As a preferred mode, the roof air quality detection data and the underbody air quality detection data both include one or more of $CO_2$ concentration, $NO_2$ concentration, $SO_2$ concentration, PM2.5 concentration, VOC concentration, and dust concentration.

As a preferred mode, a calculation method of the comprehensive roof air evaluation indicator $Q_0$ is:

$Q_0$=roof $CO_2$ concentration×$p_1$+roof $NO_2$ concentration×$p_2$+roof $SO_2$ concentration×$p_3$+roof $PM2.5$ concentration×$p_4$+roof $VOC$ concentration×$p_5$+ roof dust concentration×$p_6$;

a calculation method of the comprehensive underbody air evaluation indicator $Q_1$ is:

$Q_1$=underbody $CO_2$ concentration×$p_1$+underbody $NO_2$ concentration×$p_2$+underbody $SO_2$ concentration×$p_3$+underbody $PM2.5$ concentration×$p_4$+ underbody $VOC$ concentration×$p_5$+underbody dust concentration×$p_6$;

wherein, $p_1$, $p_2$, $p_3$, $p_4$, $p_5$, and $p_6$ are corresponding weights of pollutants.

As a preferred mode, in step 4, the calculation model of pollutant condition about roof component is trained with an LSTM deep network algorithm, wherein the weight and threshold of the LSTM deep network are obtained by optimization using quantum particle swarm with adaptive weights, including:

step A1: using a position vector of each quantum particle individual in quantum particle swarms as the weight and threshold of the LSTM deep network, and initializing the position vector parameter of the quantum particle swarm individual into a random number with a range of [−1, 1]; wherein the number of the quantum particle swarms is in a range of [30, 100], the number of particles in a quantum particle swarm is in a range of [4, 60], the maximum number of iterations is in a range of [300, 1200], the number of iterations for forming an elite swarm is in a range of [50, 200], the premature convergence determination threshold is in a range of [0.02, 0.5], and the worst particle variation ratio 6% among the swarms is in a range of [1%, 6%];

step A2: setting a fitness function, and determining a position vector of an initial optimal quantum particle individual and the number of iterations t, t=1;

substituting the weight and threshold corresponding to the position vector of the quantum particle individual into the calculation model of pollutant condition about roof component based on the LSTM deep network, determining the type of an identification vector label by using the calculation model of pollutant condition about roof component based on the LSTM deep network determined from the position vector of the quantum particle individual, and using the reciprocal of the mean square error of the output vector label and the actual vector label as a second fitness function;

step A3: calculating a colony fitness variance of each quantum particle swarm, and performing premature convergence determination;

if the colony fitness variance of the quantum particle swarm is smaller than a premature convergence determination threshold γ, mutating 6% of particles with worst fitness and a colony extreme value particle in the quantum particle swarm, and using the particle with the best fitness currently as a global optimal quantum particle individual;

step A4: determining whether to form an elite swarm;

when the number of iterations is greater than the number of iterations of the elite swarm, extracting extreme values of various swarms through information sharing between the swarms to form the elite swarm, and skipping to step A8, otherwise, performing step A5;

step A5: updating particle parameters of the various swarms;

step A6: for each particle, recalculating the fitness value of the particle and comparing the fitness value of the particle with the current individual extreme value of the particle, if the fitness value of the particle is superior to the current individual extreme value of the particle, updating the individual extreme value of the particle; comparing a current colony extreme value of the global extreme value particle with the fitness value of each particle, if the fitness value of a particle is superior to the current colony extreme value, updating the global extreme value particle, assuming t=t+1, and performing step A3;

step A7: continuing to evolve the elite swarm;

step A8: determining whether the maximum number of iterations is satisfied, and if the maximum number of iterations is satisfied, exiting the process, otherwise, assuming t=t+1 and performing step B3 till the global optimal value is found; and outputting the weight and threshold of the LSTM deep network.

As a preferred mode, in step 4, the calculation model of pollutant condition about underbody component is trained with a GRU deep network algorithm, wherein the weight and threshold of the GRU deep network are obtained by optimization using a chaotic bat algorithm, including:

step B1: using the position of a bat individual as the weight and threshold of the calculation model of pollutant condition about underbody component based on the GRU deep network, initializing bat swarms, and setting parameters of the bat swarms;

wherein the size of a bat swarm is in a range of [300, 600], the maximum pulse frequency $r_0$ of the bat individual is in a range of [0.3, 0.6], the maximum pulse sound intensity $A_0$ is in a range of [0.3, 0.6], the maximum number of iterations is in a range of [200, 500], the search accuracy is in a range of [0.002, 0.2], the pulse frequency is in a range of [0, 1.8], the increased coefficient of bat search frequency is in a range of [0.04, 0.1], the sound intensity attenuation coefficient is in a range of [0.75, 0.1], the maximum number of iterations is in a range of [200, 800], and the maximum search accuracy is in a range of [0.02, 0.15];

step B2: setting a fitness function, and determining a position of an initial optimal bat individual and the number of iterations t, t=1;

substituting the weight and threshold corresponding to the position of the bat individual into the calculation model of pollutant condition about underbody component based on the GRU deep network, and obtaining a detection result by using the calculation model of pollutant condition about underbody component based on the GRU deep network determined from the position of the bat individual, and constructing a first fitness function f1(x) from the difference E between the detection result and the actual situation, f1(x)=1/(E+1);

calculating the fitness of the position of each bat individual by using the first fitness function, and using the position of the bat individual corresponding to the maximum fitness as the position of the initial optimal bat individual;

step B3: updating the speed and position of the bat individual by using a set pulse frequency; step B4: if Rand1>$r_i$, randomly disturbing the bat at the optimal individual position to generate a disturbed position of the bat individual;

wherein Rand1 is a random number uniformly distributed on [0, 1], and $r_i$ is a pulse frequency of the i-th bat;

step B5: if Rand2>$A_i$, and the fitness of the disturbed position of the bat individual is superior to the fitness of the position of the bat individual before disturbance, moving the bat individual to the disturbed position, or else keeping the bat individual at the original position;

wherein Rand2 is a random number uniformly distributed on [0, 1], and $A_i$ is a sound intensity of the i-th bat;

step B6: if the condition of step B5 is satisfied, updating the pulse frequency and pulse sound intensity of the bat individual by using the increased coefficient of bat search frequency and the sound intensity attenuation coefficient, and skipping to step B4, or else skipping to step B7;

step B7: calculating the fitness of the position of each bat individual in the current bat swarm, and performing chaotic optimization of position and speed on top m % bat individuals in descending order to obtain updated top m % bat individuals, wherein m is in a range of [4, 25]; and step B8: determining whether the maximum number of iterations or the maximum search accuracy is reached; if it is reached, selecting a global optimal bat individual from the updated top m % bat individuals according to the fitness value, and outputting the optimal weight and threshold of the calculation model of pollutant condition about underbody component based on the GRU deep network corresponding to the global optimal bat individual; otherwise, assuming t=t+1, and skipping to step B3 to continue next iteration.

Based on the same inventive concept, the present invention further provides a system for protecting the operation of a train under an air pollution environment, characterized by including: a roof air quality detection module: configured to acquire roof air quality detection data; an underbody air quality detection module: configured to acquire underbody air quality detection data;

a data transmission module: configured to transmit the acquired roof air quality detection data and underbody air quality detection data to a data processing module;

the data processing module: configured for modeling and calculating pollution levels; wherein: the modeling process includes:

solving a comprehensive roof air evaluation indicator $Q_0$ by using the roof air quality detection data, and solving a comprehensive underbody air evaluation indicator $Q_1$ by using the underbody air quality detection data;

calculating an exposure time $T_0$ of roof components under the condition of $Q_0 \geq Q$, and calculating an exposure time $T_1$ of underbody components under the condition of $Q_1 \geq Q$; wherein Q is a set health value of comprehensive air quality evaluation indicator;

training a calculation model of pollutant condition about roof component according to the following process:

simulating the operation of the train by using the calculated average concentration of each pollutant on the roof of the train during an operating time from the time leaving a departure station to a current time and $T_0$ correspondingly solved as experimental simulation conditions to obtain a pollution level $G_0$ of the roof components under different experimental simulation conditions, wherein the pollution grade of the roof components is classified as G levels; and training the calculation model of pollutant condition about roof component by using the calculated average concentration of each pollutant on the roof of the train during the operating time from the time leaving the departure station to the current time and the $T_0$ correspondingly solved as an input and using $G_0$ as an output to obtain a trained calculation model of pollutant condition about roof component;

training a calculation model of pollutant condition about underbody component according to the following process:

simulating the operation of the train by using the calculated average concentration of each pollutant on the underbody of the train during the operating time from the time leaving the departure station to the current time and $T_1$ correspondingly solved as experimental simulation conditions to obtain a pollution level $G_1$ of the underbody components under different experimental simulation conditions, wherein the pollution grade of the underbody components is classified as G levels; and training the calculation model of pollutant condition about underbody component by using the calculated average concentration of each pollutant on the underbody of the train during the operating time from the time leaving the departure station to the current time and the $T_1$ correspondingly solved as an input and using $G_1$ as an output to obtain a trained calculation model of pollutant condition about underbody component;

the process of calculating pollution levels includes:

acquiring, after the train stops, roof air quality detection data and underbody air quality detection data;

by using the roof air quality detection data, solving an average concentration of each pollutant on the roof of the train during the operating time from the time leaving the departure station to the current time, a comprehensive roof air evaluation indicator $Q_0$, and an exposure time $T_0$ of the roof components under the condition of $Q_0 \geq Q$; and calling the trained calculation model of pollutant condition about roof component under the condition of $Q_0 \geq Q$ to solve a roof component pollution level;

by using the underbody air quality detection data, solving an average concentration of each pollutant on the underbody of the train during the operating time from the time leaving the departure station to the current time, a comprehensive underbody air evaluation indicator $Q_1$, and an exposure time $T_1$ of the underbody components under the condition of $Q_1 \geq Q$; and calling the trained calculation model of pollutant condition about underbody component under the condition of $Q_1 \geq Q$ to solve an underbody component pollution level;

sending the roof component pollution level and the underbody component pollution level to a platform data center;

the platform data center: configured to receive the roof component pollution level and the underbody component pollution level sent by the data processing module, and send protection instructions to a platform execution module according to the received roof component pollution level and underbody component pollution level; and the platform execution module: configured to perform the corresponding cleaning on the roof components and/or the underbody components according to the protection instructions sent by the platform data center.

As a preferred mode, both the roof air quality detection module and the underbody air quality detection module includes one or more of a $CO_2$ concentration sensor, a $NO_2$ concentration sensor, an $SO_2$ concentration sensor, a PM2.5 concentration sensor, a VOC concentration sensor, and a dust concentration sensor.

As a preferred mode, the roof air quality detection module includes one or more roof air quality detection devices, and roof air quality detection devices are respectively arranged at the head, middle part and tail of each compartment; the underbody air quality detection module includes one or more underbody air quality detection devices, and underbody air quality detection devices are respectively arranged at the head, middle part and tail of each compartment; and every three compartments share a data processing module.

As a preferred mode, the platform execution module includes a drone station on a platform and a human-computer interaction terminal, both the drone station on the platform and the human-computer interaction terminal are connected to the platform data center; the drone station on the platform includes one or more drones, and each drone is provided with a spraying and cleaning device and lighting equipment, and the human-computer interaction terminal includes an instruction receiving computer.

The present invention provides a method and system for protecting the operation of a train under an air pollution environment based on deep network models, one or more air quality detection modules are arranged on the train to acquire air quality data near a roof pantograph and an underbody running portion of the train, the acquired data is processed and analyzed, and pollution protection is performed by the combination of drone spraying and manual maintenance methods, which have the following advantages:

(1) By real-time and effective monitoring on the air quality near the roof and underbody components of the train during operation, the time when the exposed key components of the train are exposed to pollutants can be acquired, and the cleaning mode used when stopping can be guided.

(2) The monitoring point arrangement mode of comprehensive monitoring and multi-point monitoring of the roof and the underbody avoids detection errors caused by different air conditions on the roof and the underbody, and ensures the accuracy of the acquired results.

(3) Different cleaning protection strategies are selected according to the time when the roof and underbody components are exposed to pollutants, thereby reducing the adhesion and corrosion of air pollutants to the key components of the train, and prolonging the service lives of the corresponding key components of the train.

(4) The pollution condition of the key components of the train is divided into different levels, the most reasonable cleaning protection strategy is selected according to different pollution condition levels, and the combination of drone spraying and manual maintenance ensures the protection effect and liberates manpower as much as possible.

(5) The pollution condition levels of the roof and underbody components are calculated through deep networks, which ensures the effectiveness of the cleaning protection method after the train stops.

In the figures: 1 roof air quality detection module, 101 roof air quality detection device, 2 underbody air quality detection module, 201 underbody air quality detection device, 3 data transmission module, 301 wireless transmission module, 4 data processing module, 401 central computer, 5 platform data center, 501 platform computer, 6 platform execution module, 601 drone station on a platform, 6011 drone, 602 human-computer interaction terminal, 6021 instruction receiving computer.

DETAILED DESCRIPTION OF EMBODIMENTS

The present invention provides a method and system for protecting the operation of a train under an air pollution environment, which can monitor the concentration of air pollutants at exposed positions of key components on the roof and underbody of a high-speed train in real time, acquire pollution condition levels of the corresponding key components during operation by using a deep network according to the measured pollutant concentration, and select reasonable cleaning methods after parking. The pollution conditions of the key components are obtained by training the deep network, the input of a model is various measured data, and the output is pollution condition levels.

Figure 1:
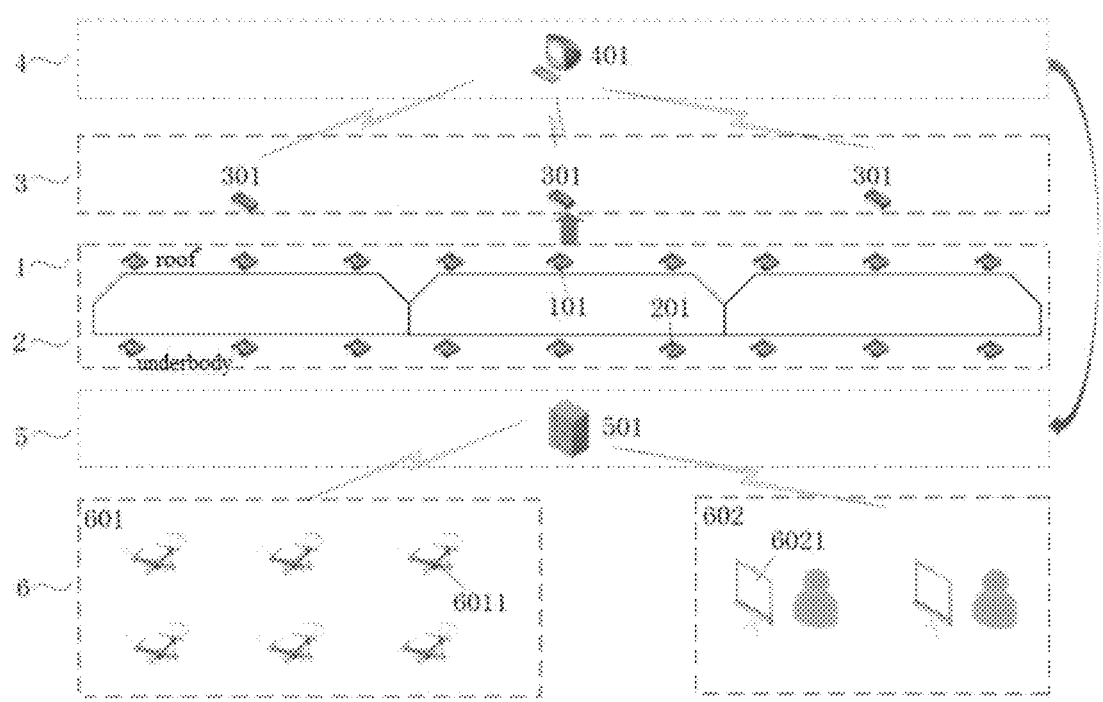
FIG. 1 is a principle diagram of an embodiment of a system according to the present invention.

As shown in FIG. 1, the entire system for protecting the operation of a train under an air pollution environment includes a roof air quality detection module 1, an underbody air quality detection module 2, a data transmission module 3, a data processing module 4, a platform data center 5 and a platform execution module 6. Details of respective modules are as follows:

Roof air quality detection module 1: this module is composed of roof air quality detection devices 101 respectively arranged on the top of each compartment. Each roof air quality detection device 101 includes a $CO_2$ concentration sensor, a $NO_2$, concentration sensor, an $SO_2$ concentration sensor, a PM2.5 concentration sensor, a VOC sensor, and a dust sensor. Roof air quality detection devices 101 are respectively arranged at the head, middle part and tail of the roof of each compartment. The data acquired by the roof air quality detection module 1 is transmitted to the data processing module 4 by the data transmission module 3.

Underbody air quality detection module 2: this module is composed of underbody air quality detection devices 201 respectively arranged on the bottom of each compartment. Each underbody air quality detection device 201 includes a CO % concentration sensor, a $NO_2$ concentration sensor, an $SO_2$ concentration sensor, a PM2.5 concentration sensor, a VOC sensor, and a dust sensor. Underbody air quality detection devices 201 are respectively arranged at the head, middle part and tail of the bottom of each compartment. The data acquired by the underbody air quality detection module 2 is transmitted to the data processing module 4 by the data transmission module 3.

Data transmission module 3: the data transmission module 3 includes wireless transmission modules 301, and each compartment is equipped with a wireless transmission device to connect the roof air quality detection module 1, the underbody air quality detection module 2 and the data processing module 4 to store the acquired data and transmit data between different modules. Considering the length of the train, the data can be transmitted through a 4G network, which is economical and simple.

Data processing module 4: a central computer 401 is equipped for every three compartments, which is defined as an air quality monitoring area and constitutes the data processing module 4. The central computer 401 is configured to receive acquired air data of key roof components and acquired air data of key underbody components acquired from three compartments within a monitoring range, perform data preprocessing and model training respectively, and output model training results in real time.

Platform data center 5: this module includes a platform computer 501, which is configured to receive pollution condition level data of key components sent by the data processing module 4 of the train, select appropriate cleaning and protection methods according to different receiving results, and send protection instructions to a drone station on a platform 601 or a human-computer interaction terminal 602.

Platform execution module 6: including the drone station on a platform 601 and the human-computer interaction terminal 602. Both the drone station on the platform 601 and the human-computer interaction terminal 602 are connected to the platform data center 5.

Drone station on a platform 601: this module is composed of protective drones 6011, a wireless instruction transceiver, and a charging platform, wherein the wireless instruction transceiver is configured to receive protection instructions from the platform computer 501, and the charging platform is configured to charge the drones 6011. The wireless instruction transceiver and the charging platform are not shown in the drawings, but they do not affect the understanding and implementation of the present invention by those skilled in the art. After receiving the protection instructions from the platform data center 5, the drones 6011 autonomously identify polluted key components (located on the roof or underbody), and perform light or deep cleaning. Each protective drone 6011 is equipped with a spraying and cleaning device and lighting equipment. Human-computer interaction terminal 602: this module includes an instruction receiving computer 6021, which is configured to receive manual maintenance instructions sent by the station data center 5 and display the same on an interactive interface.

Figure 2:
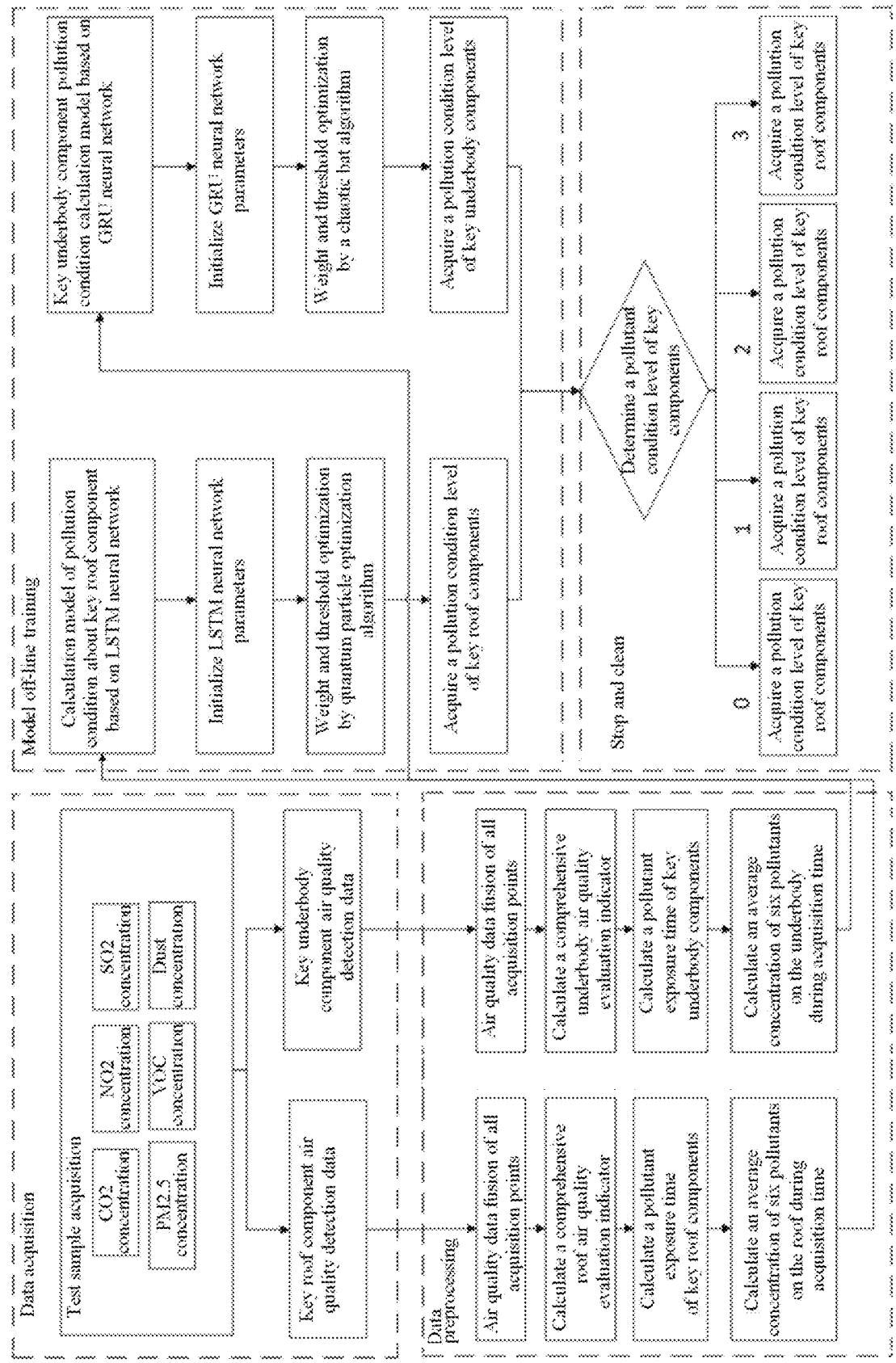
FIG. 2 is a flowchart of an embodiment of a method according to the present invention.

As shown in FIG. 2, the entire method for protecting the operation of a train under an air pollution environment includes two processes: an off-line training process and an on-line protection process when the train stops.

Off-Line Training Process:

The method of the present invention first acquires air pollutant concentration information of a space where key roof and underbody components are located, and then sends the acquired data to the central computer 401 in a corresponding detection area for data preprocessing and model training. The training model includes two deep network models, which are configured to acquire pollution condition levels of key components according to the measured pollutant concentration. The entire off-line process is described as follows:

1. Air Quality Data Acquisition of the Space where the Key Roof and Underbody Components are Located Different pollutant concentration is acquired by the roof air quality detection device 101 and the underbody air quality detection device 201, wherein the acquired roof air quality detection data is expressed as [t, $I_{CO_2}$, $I_{NO_2}$, $I_{SO_2}$, $I_{pm\,2.5}$, $I_{voc}$, $I_{dust}$], and the underbody air quality detection data is expressed as [t, $O_{CO_2}$, $O_{NO_2}$, $O_{SO_2}$, $O_{PM\,2.5}$, $O_{voc}$, $O_{dust}$]. In order to distinguish the data acquired by the air quality detection devices at different positions in different compartments, the format of the final roof air quality data sent by the wireless transmission module 301 is [t, $I_{CO_2}$, $I_{NO_2}$, $I_{SO_2}$, $I_{pm\,2.5}$, $I_{voc}$, $I_{dust}$, n, m, 0] and [t, $O_{CO_2}$, $O_{NO_2}$, $O_{SO_2}$, $O_{PM\,2.5}$, $O_{voc}$, $O_{dust}$, n, m, 1], where t represents an acquisition time point of the group of data; n represents a compartment number; m represents a number of the air quality detection device, m=1, 2, 3; 0/1 is a data type identification code, 0 represents that the group of data is roof air quality detection data, and 1 represents that the group of data is underbody air quality detection data.

2. Data Preprocessing

The data of the roof air quality detection device 101 and the underbody air quality detection device 201 is transmitted to the central computer 401 of the data processing module 4 via the wireless transmission module 301 for preprocessing the acquired data. The entire data preprocessing steps are as follows:

(1) According to the 0/1 identification code and m value of each group of data, the acquired data of air quality detection points at all key roof components and the detected data of air quality detection points at all key underbody components are averaged, and the concentration of six pollutants is normalized to finally obtain total roof air quality detection data [t, $O_{CO_2 total}$, $O_{NO_2 total}$, $O_{SO_2 total}$, $O_{pm\,2.5 total}$, $O_{voctotal}$, $O_{dusttotal}$, n, 0] and total underbody air quality detection data [t, $O_{CO_2 total}$, $O_{NO_2 total}$, $O_{SO_2 total}$, $O_{pm\,2.5 total}$, $O_{voctotal}$, $O_{dusttotal}$, n, 1] of a target detected compartment.

(2) A comprehensive air quality evaluation indicator is calculated, and a calculation method for the comprehensive air quality evaluation indicator is defined as:

$$Q = CO_2\text{ concentration} \times p_1 + NO_2\text{ concentration} \times p_2 + SO_2\text{ concentration} \times p_3 + PM2.5\text{ concentration} \times p_4 + VOC\text{ concentration} \times p_5 + \text{dust concentration} \times p_6$$

Where p represents weights of concentration of different pollutants, $p_1=0.1$, $p_2=0.1$, $p_3=0.1$, $p_4=0.3$, $p_5=0.2$, and $p_6=0.2$. Then, the final roof and underbody air quality detection data obtained in step (1) is substituted into the above equation for the calculation to obtain a comprehensive roof air evaluation indicator $Q_0$ and a comprehensive underbody air evaluation indicator $Q_1$.

(3) A health value of comprehensive air quality evaluation indicator is set to be Q, time points at which the conditions of $Q_0 \geq Q$ and $Q_1 \geq Q$ are met are respectively calculated, and an exposure time T0 of key roof components in pollutants under the condition of $Q_0 \geq Q$ and an exposure time $T_1$ of key underbody components in pollutants under the condition of $Q_1 \geq Q$ are acquired.

(4) Average concentration $[I_{CO_2average}, I_{NO_2average}, I_{SO_2average}, I_{pm\ 2.5average}, I_{vocaverage}, I_{dustaverage}, n, 0]$ and $[O_{CO_2average}, O_{NO_2average}, O_{SO_2average}, O_{pm\ 2.5average}, O_{vocaverage}, O_{dustaverage}, n, 1]$ of six pollutants during the operating time of the train from the time leaving the departure station to the current time point is calculated.

3. Training of Calculation Model of Pollutant Condition about Key Train Component (1) Training of a Calculation Model of Pollutant Condition about Roof Component Roof air quality data is measured under outdoor experimental conditions, 1000 groups of different degrees of roof air quality data are picked, then indoor simulation operation is performed on each group of experimental data among the 1000 groups under experimental simulation conditions to obtain pollution conditions of a pantograph under different conditions, and four pollution levels 0, 1, 2, and 3 are set according to the overall pollution condition.

The calculation model of pollutant condition about roof component is trained using a long short term memory (LSTM) deep network. The input of the model training is average roof air quality detection data and key roof component pollutant exposure time $[I_{CO_2average}, I_{NO_2average}, I_{SO_2average}, I_{pm\ 2.5average}, I_{vocaverage}, I_{dustaverage}, T_0]$, the output is the pollution condition levels 0, 1, 2, and 3 of the pantograph acquired under the simulated experimental conditions, thereby obtaining the calculation model of pollutant condition about roof component based on the LSTM deep network.

The input layer of the LSTM deep network includes 7 nodes, the output layer includes 1 node, the maximum number of iterations in the training process is set to be 1200, and the learning rate in the training is 0.01.

In the calculation model of pollutant condition about roof component based on the LSTM deep network, the weight and threshold of the LSTM deep network are obtained by optimization using quantum particle swarm with adaptive weights. The process is as follows:

Step A1: using a position vector of each quantum particle individual in quantum particle swarms as the weight and threshold of the LSTM deep network, the position vector parameter of the quantum particle swarm individual is initialized into a random number in the range of $[-1, 1]$; The number of the quantum particle swarms is in a range of [30, 100], the number of particles in a quantum particle swarm is in a range of [4, 60], the maximum number of iterations is in a range of [300, 1200], the number of iterations for forming an elite swarm is in a range of [50, 200], the premature convergence determination threshold is in a range of [0.02, 0.5], and the worst particle variation ratio 6% among the swarms is in a range of [1%, 6%];

Step A2: a fitness function is set, and a position vector of an initial optimal quantum particle individual and the number of iterations t are determined, t=1;

The weight and threshold corresponding to the position vector of the quantum particle individual are substituted into the calculation model of pollutant condition about roof component based on the LSTM deep network, the type of an identification vector label is determined by using the calculation model of pollutant condition about roof component based on the LSTM deep network determined from the position vector of the quantum particle individual, and the reciprocal of the mean square error of the output vector label and the actual vector label is used as a second fitness function;

Step A3: a colony fitness variance of each quantum particle swarm is calculated, and premature convergence determination is performed;

If the swarm fitness variance of the quantum particle swarm is smaller than a premature convergence determination threshold γ, 6% of particles with worst fitness and a colony extreme value particle in the quantum particle swarm are mutated, and the particle individual with the best fitness currently are used as a global optimal quantum particle individual;

Step A4: whether to form an elite swarm is determined;

When the number of iterations is greater than the number of iterations of the elite swarm, extreme values of various swarms are extracted through information sharing between the swarms to form the elite swarm, and skipping to step A8, otherwise, step A5 is performed;

Step A5: particle parameters of various swarms are updated;

Step A6: for each particle, the fitness value of the particle is recalculated, and the fitness value of the particle is compared with the current individual extreme value of the particle, if the fitness value of the particle is superior to the current individual extreme value of the particle, the individual extreme value of the particle is updated; a current colony extreme value of the global extreme value particle is compared with the fitness value of each particle, if the fitness value of a particle is superior to the current colony extreme value, the global extreme value particle is updated, t=t+1 is assumed, and skipping to step A3;

Step A7: the elite swarm continues to be evolved;

Step A8: whether the maximum number of iterations is satisfied is determined, and if the maximum number of iterations is satisfied, the process exits, otherwise, t=t+1 is assumed and skipping to step B3 till the global optimal value is found; and the weight and threshold of the LSTM deep network are output.

(2) Training of a Calculation Model of Pollutant Condition about Underbody Component Underbody air quality data is measured under outdoor experimental conditions, 1000 groups of different degrees of underbody air quality data are picked, then indoor simulation operation is performed on each group of experimental data among the 1000 groups under experimental simulation conditions to obtain pollution conditions of a running portion under different conditions, and four pollution levels 0, 1, 2, and 3 are set according to the overall pollution condition.

The calculation model of pollutant condition about underbody component is trained using a gated recurrent unit (GRU) deep network. The input of the model training is average underbody air quality detection data and key underbody component pollutant exposure time $[O_{CO_2average}, O_{NO_2average}, O_{SO_2average}, O_{pm\ 2.5average}, O_{vocaverage}, O_{dustaverage}, T_1]$, the output is the pollution condition levels 0, 1, 2, and 3 of the running portion acquired under the simulated experimental conditions, thereby obtaining the calculation model of pollutant condition about underbody component based on the GRU deep network.

In the calculation model of pollutant condition about underbody component based on the GRU deep network, the number of input layer nodes is 7, the number of hidden layer nodes is 5, and the number of output layer nodes is 1; the maximum number of iterations in the training process is set to be 800, the learning rate in the training is 0.01, and the threshold is 0.06.

The weight and threshold of the calculation model of pollutant condition about underbody component based on the GRU deep network are subjected to optimization selection through a chaotic bat algorithm. The process is as follows:

Step B1: using the position of a bat individual as the weight and threshold of the calculation model of pollutant condition about underbody component based on the GRU deep network, bat swarms are initialized, and parameters of the bat swarms are set;

The size of a bat swarm is in a range of [300, 600], the maximum pulse frequency $r_0$ of the bat individual is in a range of [0.3, 0.6], the maximum pulse sound intensity $A_0$ is in a range of [0.3, 0.6], the maximum number of iterations is in a range of [200, 500], the search accuracy is in a range of [0.002, 0.2], the pulse frequency is in a range of [0, 1.8], the increased coefficient of bat search frequency is in a range of [0.04, 0.1], the sound intensity attenuation coefficient is in a range of [0.75, 0.1], the maximum number of iterations is in a range of [200, 800], and the maximum search accuracy is in a range of [0.02, 0.15];

Step B2: a fitness function is set, and a position of an initial optimal bat individual and the number of iterations t are determined, t=1;

the weight and threshold corresponding to the position of the bat individual are substituted into the calculation model of pollutant condition about underbody component based on the GRU deep network, a detection result is obtained by using the calculation model of pollutant condition about underbody component based on the GRU deep network determined from the position of the bat individual, and a first fitness function f1(x) is constructed from the difference E between the detection result and the actual situation, f1(x)=1/(E+1);

The fitness of the position of each bat individual is calculated by using the first fitness function, and the position of the bat individual corresponding to the maximum fitness is used as a position of the initial optimal bat individual;

Step B3: the speed and position of the bat individual are updated by using a set pulse frequency;

Step B4: if Rand1>$r_i$, the bat at the optimal individual position is randomly disturbed to generate a disturbed position of the bat individual;

where Rand1 is a random number uniformly distributed on [0, 1], and $r_i$ is a pulse frequency of the i-th bat;

Step B5: if Rand2>$A_i$ and the fitness of the disturbed position of the bat individual is superior to the fitness of the position of the bat individual before disturbance, the bat individual is moved to the disturbed position, or else the bat individual is kept at the original position;

where Rand2 is a random number uniformly distributed on [0, 1], and $A_i$ is a sound intensity of the i-th bat;

Step B6: if the condition of step B5 is satisfied, the pulse frequency and pulse sound intensity of the bat individual are updated by using the increased coefficient of bat search frequency and the sound intensity attenuation coefficient, and the process skips to step B4, or else skips to step B7;

Step B7: the fitness of the position of each bat individual in the current bat swarm is calculated, and chaotic optimization of position and speed is performed on top m % bat individuals in descending order to obtain updated top m % bat individuals, wherein m is in a range of [4, 25];

Step B8: whether the maximum number of iterations or the maximum search accuracy is reached is determined; if it is reached, a global optimal bat individual is selected from the updated top m % bat individuals according to the fitness value, and the optimal weight and threshold of the calculation model of pollutant condition about underbody component based on the GRU deep network corresponding to the global optimal bat individual are output; otherwise, t=t+1 is assumed, and step B3 is performed to continue next iteration.

On-Line Protection Process when the Train Stops:

(1) After the train stops, for a certain detected compartment, the roof air quality detection module 1 and the underbody air quality detection module 2 acquire data, and the wireless transmission module 301 transmits the data to the data processing module 4 for preprocessing to obtain an average concentration of six pollutants on the roof and underbody of the train during the operation time from the time leaving the departure station to the current time, a comprehensive roof air quality evaluation indicator $Q_0$ and a comprehensive underbody air quality evaluation indicator $Q_1$, as well as a pollutant exposure time $T_0$ of key roof components and a pollutant exposure time $T_1$ of key underbody components.

(2) The data processing module 4 calculates a pollution condition level 0/1/2/3 of the key roof component through the trained calculation model of pollutant condition about roof component based on the LSTM deep network, and the data processing module 4 calculates a pollution condition level 0/1/2/3 of the key underbody component through the trained calculation model of pollutant condition about underbody component based on the GRU deep network. The data processing module 4 transmits the pollutant condition levels of the roof and underbody to the platform data center 5.

(3) When the pollution level of the key components on the roof or underbody is 0, the key components of the train are considered to be not polluted, and cleaning is not required when the train stops; when the pollution level of the key components on the roof or underbody is 1, the pollution condition of the key components of the train is considered to be relatively light, and the drone station on the platform 601 is called for light cleaning; when the pollution level of the key components on the roof or underbody is 2, the pollution condition of the key components of the train is considered to be normal, and the drone station on the platform 601 is called for deep cleaning; and when the pollution level of the key components on the roof or underbody is 3, the pollution condition of the key components of the train is considered to be serious, and a cleaning instruction is sent to the human-computer interaction terminal 602 to apply for manual cleaning.

(4) The drone 6011 on the platform identifies the pantograph and running portion of the train through a camera and hovers; after the drone 6011 operates and hovers for more than 5 s, the spraying and cleaning device operates automatically, wherein the operating time of the spraying and cleaning device is 1 min during light cleaning, and the operating time of the spraying and cleaning device is 3 min during the deep cleaning.

The present application further provides a method for solving a roof component pollution level and an underbody component pollution level about a train under an air pollution environment, wherein the method comprises the following steps.

step 1, acquiring multiple groups of roof air quality detection data and underbody air quality detection data, and calculating an average concentration of each pollutant on the roof and underbody of the train during an operating time from the time leaving a departure station to a current time:

step 2, solving a comprehensive roof air evaluation indicator $Q_0$ by using the roof air quality detection data in step 1, and solving a comprehensive underbody air evaluation indicator $Q_1$ by using the underbody air quality detection data in step 1;

step 3, calculating an exposure time $T_0$ of roof components under the condition of $Q_0 \geq Q$, and calculating an exposure time $T_1$ of underbody components under the condition of $Q_1 \geq Q$; wherein Q is a set health value of comprehensive air quality evaluation indicator;

step 4, training a calculation model of pollutant condition about roof component according to the following method;

simulating the operation of the train by using the average concentration, calculated in step 1, of each pollutant on the roof of the train during the operating time from the time leaving the departure station to the current time and the $T_0$ correspondingly solved in step 3 as experimental simulation conditions to obtain a pollution level $G_0$ of the roof components under different experimental simulation conditions, wherein the pollution grade of the roof components is classified as G levels; and training the calculation model of pollutant condition about roof component by using the average concentration, calculated in step 1, of each pollutant on the roof of the train during the operating time from the time leaving the departure station to the current time and the $T_0$ correspondingly solved in step 3 as an input and using $G_0$ as an output to obtain a trained calculation model of pollutant condition about roof component;

training a calculation model of pollutant condition about underbody component according to the following method:

simulating the operation of the train by using the average concentration, calculated in step 1, of each pollutant on the underbody of the train during the operating time from the time leaving the departure station to the current time and the T correspondingly solved in step 3 as experimental simulation conditions to obtain a pollution level $G_1$ of the underbody components under different experimental simulation conditions, wherein the pollution grade of the underbody components is classified as G levels; and training the calculation model of pollutant condition about underbody component by using the average concentration, calculated in step 1. of each pollutant on the underbody of the train during the operating time from the time leaving the departure station to the current time and the $T_1$ correspondingly solved in step 3 as an input and using Ci as an output to obtain a trained calculation model of pollutant condition about underbody component;

step 5, acquiring, after the train stops, roof air quality detection data and underbody air quality detection data;

step 6, by using the roof air quality detection data in step 5. solving an average concentration of each pollutant on the roof of the train during the operating time from the time leaving the departure station to the current time, a comprehensive roof air evaluation indicator $Q_0$. and an exposure time $T_0$ of the roof components under the condition of $Q_0 \geq Q$; and calling the trained calculation model of pollutant condition about roof component under the condition of $Q_0 \geq Q$ to solve a roof component pollution level; and by using the underbody air quality detection data in step 5. solving an average concentration of each pollutant on the underbody of the train during the operating time from the time leaving the departure station to the current time, a comprehensive underbody air evaluation indicator $Q_1$, and an exposure time $T_1$ of the underbody components under the condition of $Q_1 \geq Q$; and calling the trained calculation model of pollutant condition about underbody component under the condition of $Q_1 \geq Q$ to solve an underbody component pollution level.

The embodiments of the present invention are described above with reference to the drawings, but the present invention is not limited to the specific embodiments. The specific embodiments described above are merely illustrative but not restrictive. Many forms may also be made by those of ordinary skill in the art under the enlightenment of the present invention without departing from the purpose of the present invention and the scope of the claims, and these forms fall into the scope of the present invention.

The invention claimed is:

1. A method for protecting the operation of a train under an air pollution environment, comprising the following steps:

step 1, acquiring multiple groups of roof air quality detection data and underbody air quality detection data, and calculating an average concentration of each pollutant on the roof and underbody of the train during an operating time from the time leaving a departure station to a current time;

step 2, solving a comprehensive roof air evaluation indicator $Q_0$ by using the roof air quality detection data in step 1, and solving a comprehensive underbody air evaluation indicator $Q_1$ by using the underbody air quality detection data in step 1;

step 3, calculating an exposure time $T_0$ of a roof component under the condition of $Q_0 > Q$, and calculating an exposure time $T_1$ of an underbody component under the condition of $Q_1 > Q$; wherein Q is a set health value of comprehensive air quality evaluation indicator;

step 4, training a calculation model of pollutant condition for the roof component according to the following method:

simulating the operation of the train by using the average concentration, calculated in step 1, of each pollutant on the roof of the train during the operating time from the time leaving the departure station to the current time and the $T_0$ correspondingly solved in step 3 as experimental simulation conditions to obtain a pollution level $G_0$ of the roof component under different experimental simulation conditions; and training the calculation model of pollutant condition for the roof component by using the average concentration, calculated in step 1, of each pollutant on the roof of the train during the operating time from the time leaving the departure station to the current time and the $T_0$ correspondingly solved in step 3 as an input and using $G_0$ as an output to obtain a trained calculation model of pollutant condition for the roof component;

training a calculation model of pollutant condition for the underbody component according to the following method:

simulating the operation of the train by using the average concentration, calculated in step 1, of each pollutant on the underbody of the train during the operating time from the time leaving the departure station to the current time and the $T_1$ correspondingly solved in step 3 as experimental simulation conditions to obtain a pollution level $G_1$ of the underbody component under a different experimental simulation condition; and training the calculation model of pollutant condition for the underbody component by using the average concentration, calculated in step 1, of each pollutant on the underbody of the train during the operating time from the time leaving the departure station to the current time and the $T_1$ correspondingly solved in step 3 as an input and using $G_1$ as an output to obtain a trained calculation model of pollutant condition for the underbody component;

step 5, acquiring, after the train stops, roof air quality detection data and underbody air quality detection data;

step 6, by using the roof air quality detection data in step 5, solving an average concentration of each pollutant on the roof of the train during the operating time from the time leaving the departure station to the current time when the roof air quality detection data and underbody air quality detection data are acquired after the train stops, solving a comprehensive roof air evaluation indicator $Q_0$, and calculating an exposure time $T_0$ of the roof component under the condition of $Q_0>Q$; and calling the trained calculation model of pollutant condition for the roof component under the condition of $Q_0>Q$ to solve a roof component pollution level; and by using the underbody air quality detection data in step 5, solving an average concentration of each pollutant on the underbody of the train during the operating time from the time leaving the departure station to the current time when the roof air quality detection data and underbody air quality detection data are acquired after the train stops, solving a comprehensive underbody air evaluation indicator $Q_1$, and calculating an exposure time $T_1$ of the underbody component under the condition of $Q_1>Q$; and calling the trained calculation model of pollutant condition for the underbody component under the condition of $Q_1>Q$ to solve an underbody component pollution level; and step 7, performing corresponding cleaning on the roof component according to the pollution level, solved in step 6, of the roof component; and performing corresponding cleaning on the underbody component according to the pollution level, solved in step 6, of the underbody component.

2. The method for protecting the operation of the train under an air pollution environment according to claim 1, wherein the roof air quality detection data and the underbody air quality detection data both comprise one or more of $CO_2$ concentration, $NO_2$ concentration, $SO_2$ concentration, PM2.5 concentration, VOC concentration, and dust concentration.

3. The method for protecting the operation of the train under an air pollution environment according to claim 1, wherein the roof air quality detection data and/or the underbody air quality detection data are obtained from multiple monitoring sites.

4. The method for protecting the operation of the train under an air pollution environment according to claim 1, wherein a calculation method of the comprehensive roof air evaluation indicator $Q_0$ is:

$Q_0$=roof $CO_2$ concentration×$p_1$+roof $NO_2$ concentration×$p_2$+roof $SO_2$ concentration×$p_3$+roof PM2.5 concentration×$p_4$+roof VOC concentration×$p_5$+ roof dust concentration×$p_6$;

a calculation method of the comprehensive underbody air evaluation indicator $Q_1$ is:

$Q_1$=underbody $CO_2$ concentration×$p_1$+underbody $NO_2$ concentration×$p_2$+underbody $SO_2$ concentration×$p_3$+underbody PM2.5 concentration×$p_4$+ underbody VOC concentration×$p_5$+underbody dust concentration×$p_6$;

wherein, $p_1$, $p_2$, $p_3$, $p_4$, $p_5$ and $p_6$ are corresponding weights of pollutants.

5. The method for protecting the operation of the train under an air pollution environment according to claim 1, wherein in step 4, the calculation model of pollutant condition for the roof component is trained with an LSTM deep network algorithm, wherein the weight and threshold of the LSTM deep network are obtained by optimization using quantum particle swarm with adaptive weights, comprising:

step A1: using a position vector of each quantum particle individual in quantum particle swarms as the weight and threshold of the LSTM deep network, and initializing the position vector parameter of the quantum particle swarm individual into a random number with a range of [−1, 1];

wherein the number of the quantum particle swarms is in a range of [30, 100], the number of particles in a quantum particle swarm is in a range of [4, 60], the maximum number of iterations is in a range of [300, 1200], the number of iterations for forming an elite swarm is in a range of [50, 200], the premature convergence determination threshold is in a range of [0.02, 0.5], and the worst particle variation ratio 6% among the swarms is in a range of [1%, 6%];

step A2: setting a fitness function, and determining a position vector of an initial optimal quantum particle individual and the number of iterations t, t=1;

substituting the weight and threshold corresponding to the position vector of the quantum particle individual into the calculation model of pollutant condition for the roof component based on the LSTM deep network, determining the type of an identification vector label by using the calculation model of pollutant condition for the roof component based on the LSTM deep network determined from the position vector of the quantum particle individual, and using the reciprocal of the mean square error of the output vector label and the actual vector label as a second fitness function;

step A3: calculating a colony fitness variance of each quantum particle swarm, and performing premature convergence determination;

if the colony fitness variance of the quantum particle swarm is smaller than a premature convergence determination threshold γ, mutating δ% of particles with worst fitness and a colony extreme value particle in the quantum particle swarm, and using the particle with the best fitness currently as a global optimal quantum particle individual;

step A4: determining whether to form an elite swarm;

when the number of iterations is greater than the number of iterations for forming the elite swarm, extracting extreme values of various swarms through information sharing between the swarms to form the elite swarm, and skipping to step A7, otherwise, performing step A5;

step A5: updating particle parameters of the various swarms;

step A6: for each particle, recalculating the fitness value of the particle and comparing the fitness value of the particle with the current individual extreme value of the particle, if the fitness value of the particle is superior to the current individual extreme value of the particle, updating the individual extreme value of the particle; comparing a current colony extreme value of the global extreme value particle with the fitness value of each particle, if the fitness value of a particle is superior to the current colony extreme value, updating the global extreme value particle, assuming t=t+1, and performing step A3;

step A7: determining whether the maximum number of iterations is satisfied, and if the maximum number of iterations is satisfied, exiting the process, otherwise, assuming t=t+1 and performing step A3 till the global optimal value is found; and outputting the weight and threshold of the LSTM deep network.

6. The method for protecting the operation of the train under an air pollution environment according to claim 1, wherein in step 4, the calculation model of pollutant condition for the underbody component is trained with a GRU deep network algorithm, wherein the weight and threshold of the GRU deep network are obtained by optimization using a chaotic bat algorithm, comprising:

step B1: using the position of a bat individual as the weight and threshold of the calculation model of pollutant condition for the underbody component based on the GRU deep network, initializing bat swarms, and setting parameters of the bat swarms;

wherein the size of a bat swarm is in a range of [300, 600], the maximum pulse frequency r0 of the bat individual is in a range of [0.3, 0.6], the maximum pulse sound intensity A0 is in a range of [0.3, 0.6], the search accuracy is in a range of [0.002, 0.2], the pulse frequency is in a range of [0, 1.8], the increased coefficient of bat search frequency is in a range of [0.04, 0.1], the sound intensity attenuation coefficient is in a range of [0.75, 0.1], the maximum number of iterations is in a range of [200, 800], and the maximum search accuracy is in a range of [0.02, 0.15];

step B2: setting a fitness function, and determining a position of an initial optimal bat individual and the number of iterations t, t=1; substituting the weight and threshold corresponding to the position of the bat individual into the calculation model of pollutant condition for the underbody component based on the GRU deep network, obtaining a detection result by using the calculation model of pollutant condition for the underbody component based on the GRU deep network determined from the position of the bat individual, and constructing a first fitness function f1(E) from the difference E between the detection result and the actual situation, f1(E)=1/(E+1);

calculating the fitness of the position of each bat individual by using the first fitness function, and using the position of the bat individual corresponding to the maximum fitness as a position of the initial optimal bat individual;

step B3: updating the speed and position of the bat individual by using a set pulse frequency;

step B4: if Rand1>$r_i$, randomly disturbing the bat at the optimal individual position to generate a disturbed position of the bat individual;

wherein Rand1 is a random number uniformly distributed on [0, 1], and $r_i$ is a pulse frequency of the i-th bat;

step B5: if Rand2>$A_i$, and the fitness of the disturbed position of the bat individual is superior to the fitness of the position of the bat individual before disturbance, moving the bat individual to the disturbed position, or else keeping the bat individual at the original position;

wherein Rand2 is a random number uniformly distributed on [0, 1], and $A_i$ is a sound intensity of the i-th bat;

step B6: if the condition of step B5 is satisfied, updating the pulse frequency and pulse sound intensity of the bat individual by using the increased coefficient of bat search frequency and the sound intensity attenuation coefficient, and returning to step B4, or else continuing to step B7;

step B7: calculating the fitness of the position of each bat individual in the current bat swarm, and performing chaotic optimization of position and speed on top m % bat individuals in descending order to obtain updated top m % bat individuals, wherein m is in a range of [4, 25]; and step B8: determining whether the maximum number of iterations or the maximum search accuracy is reached; if it is reached, selecting a global optimal bat individual from the updated top m % bat individuals according to the fitness value, and outputting the optimal weight and threshold of the calculation model of pollutant condition for the underbody component based on the GRU deep network corresponding to the global optimal bat individual; otherwise, assuming t=t+1, and performing step B3 to continue next iteration.

7. A system for protecting the operation of a train under an air pollution environment, comprising:

a roof air quality detection module configured to acquire roof air quality detection data;

an underbody air quality detection module configured to acquire underbody air quality detection data;

a data transmission module configured to transmit the acquired roof air quality detection data and underbody air quality detection data to a data processing module;

the data processing module configured for modeling and calculating pollution levels;

wherein the modeling process comprises:

calculating an average concentration of each pollutant on the roof of the train during an operating time from the time leaving a departure station to a current time by using the roof air quality detection data, and calculating an average concentration of each pollutant on the underbody of the train during the operating time from the time leaving the departure station to the current time by using the underbody air quality detection data;

solving a comprehensive roof air evaluation indicator $Q_0$ by using the roof air quality detection data, and solving a comprehensive underbody air evaluation indicator $Q_1$ by using the underbody air quality detection data;

calculating an exposure time $T_0$ of a roof component under the condition of $Q_0$>Q and calculating an exposure time $T_1$ of an underbody component under the condition of $Q_1$>Q; wherein Q is a set health value of comprehensive air quality evaluation indicator;

training a calculation model of pollutant condition for the roof component according to the following process:

simulating the operation of the train by using the calculated average concentration of each pollutant on the roof of the train during an operating time from the time leaving a departure station to a current time and $T_0$ correspondingly solved as experimental simulation conditions to obtain a pollution level $G_0$ of the roof component under a different experimental simulation condition; and training the calculation model of pollutant condition for the roof component by using the calculated average concentration of each pollutant on the roof of the train during the operating time from the time leaving the departure station to the current time and the $T_0$ correspondingly solved as an input and using $G_0$ as an output to obtain a trained calculation model of pollutant condition for the roof component;

training a calculation model of pollutant condition for the underbody component according to the following process:

simulating the operation of the train by using the calculated average concentration of each pollutant on the underbody of the train during the operating time from the time leaving the departure station to the current time and $T_1$ correspondingly solved as experimental simulation conditions to obtain a pollution level $G_1$ of the underbody component under the different experimental simulation condition; and training the calculation model of pollutant condition for the underbody component by using the calculated average concentration of each pollutant on the underbody of the train during the operating time from the time leaving the departure station to the current time and the $T_1$ correspondingly solved as an input and using $G_1$ as an output to obtain a trained calculation model of pollutant condition for the underbody component;

the process of calculating pollution levels comprises:

acquiring, after the train stops, roof air quality detection data and underbody air quality detection data;

by using the roof air quality detection data, solving an average concentration of each pollutant on the roof of the train during the operating time from the time leaving the departure station to the current time when the roof air quality detection data and underbody air quality detection data are acquired after the train stops, solving a comprehensive roof air evaluation indicator $Q_0$, and calculating an exposure time $T_0$ of the roof component under the condition of $Q_0 > Q$; and calling the trained calculation model of pollutant condition for the roof component under the condition of $Q_0 > Q$ to solve a roof component pollution level;

by using the underbody air quality detection data in step 5, solving an average concentration of each pollutant on the underbody of the train during the operating time from the time leaving the departure station to the current time when the roof air quality detection data and underbody air quality detection data are acquired after the train stops, solving a comprehensive underbody air evaluation indicator $Q_1$, and calculating an exposure time $T_1$ of the underbody component under the condition of $Q_1 > Q$; and calling the trained calculation model of pollutant condition for the underbody component under the condition of $Q_1 > Q$ to solve an underbody component pollution level;

sending the roof component pollution level and the underbody component pollution level to a platform data center;

the platform data center configured to receive the roof component pollution level and the underbody component pollution level sent by the data processing module, and send protection instructions to a platform execution module according to the received roof component pollution level and underbody component pollution level; and the platform execution module configured to perform the corresponding cleaning on the roof component and/or the underbody component according to the protection instructions sent by the platform data center.

8. The system for protecting the operation of the train under an air pollution environment according to claim 7, wherein both the roof air quality detection module and the underbody air quality detection module comprise one or more of a $CO_2$ concentration sensor, a $NO_2$ concentration sensor, a $SO_2$ concentration sensor, a PM2.5 concentration sensor, a VOC concentration sensor, and a dust concentration sensor.

9. The system for protecting the operation of the train under an air pollution environment according to claim 7, wherein the roof air quality detection module comprises one or more roof air quality detection devices, and a roof air quality detection device is arranged at a head, a middle part and a tail of each compartment, respectively;

the underbody air quality detection module comprises one or more underbody air quality detection devices, and an underbody air quality detection device is arranged at the head, middle part and tail of each compartment, respectively; and every three compartments share a data processing module.

10. The system for protecting the operation of the train under an air pollution environment according to claim 7, wherein the platform execution module comprises a drone station on a platform and a human-computer interaction terminal, both the drone station on the platform and the human-computer interaction terminal are connected to the platform data center; the drone station on the platform comprises one or more drones, and each drone is provided with a spraying and cleaning device and lighting equipment, and the human-computer interaction terminal comprises an instruction receiving computer.

* * * * *